(12) United States Patent
Matsumoto

(10) Patent No.: US 6,777,181 B2
(45) Date of Patent: Aug. 17, 2004

(54) METHOD FOR SEPARATING AND COLLECTING NUCLEIC ACIDS

(75) Inventor: Kazuko Matsumoto, Chiba (JP)

(73) Assignee: Nisshinbo Industries, Inc., Tokyo (JP)

(*) Notice: Subject to any disclaimer, the term of this patent is extended or adjusted under 35 U.S.C. 154(b) by 0 days.

(21) Appl. No.: 09/771,439

(22) Filed: Jan. 26, 2001

(65) Prior Publication Data

US 2002/0006666 A1 Jan. 17, 2002

(30) Foreign Application Priority Data

Jan. 26, 2000 (JP) .......................................... 2000-21842

(51) Int. Cl.⁷ ........................... C12Q 1/68; C07H 21/04
(52) U.S. Cl. ..................... 435/6; 435/287.2; 435/288.3; 435/288.4; 435/288.7; 536/25.4
(58) Field of Search ...................... 435/6, 287.2, 288.3, 435/288.4, 288.7; 536/25.4, 23.1, 24.2, 24.3, 24.31, 24.32, 25.3

(56) References Cited

U.S. PATENT DOCUMENTS

| | | | | |
|---|---|---|---|---|
| 5,449,604 A | * | 9/1995 | Schellenberg et al. | ......... 435/6 |
| 5,605,662 A | * | 2/1997 | Heller et al. | |
| 5,610,287 A | | 3/1997 | Nikiforov et al. | |
| 5,635,045 A | * | 6/1997 | Alam | |
| 5,760,130 A | | 6/1998 | Johnston et al. | |
| 5,800,992 A | * | 9/1998 | Fodor et al. | ................. 435/6 |
| 5,824,477 A | * | 10/1998 | Stanley | |
| 6,007,987 A | * | 12/1999 | Cantor et al. | |
| 6,017,742 A | * | 1/2000 | Takenishi et al. | ........... 325/180 |
| 6,054,439 A | * | 4/2000 | Szyf et al. | ..................... 514/44 |
| 6,150,102 A | * | 11/2000 | Mills, Jr. | ....................... 435/6 |
| 6,355,423 B1 | * | 3/2002 | Rothberg et al. | |
| 6,432,650 B1 | * | 8/2002 | Christian et al. | .............. 435/6 |
| 6,472,173 B1 | * | 10/2002 | Ford et al. | ................. 435/69.1 |

FOREIGN PATENT DOCUMENTS

| | | |
|---|---|---|
| EP | 0 533 952 A1 | 3/1993 |
| EP | 0 710 666 A1 | 5/1996 |
| JP | 4-325092 | 11/1992 |
| WO | WO 99/20640 | 4/1999 |

OTHER PUBLICATIONS

Lamture. et al. "Direct Detection of Nucleic Acid Hybridization on the Surface of a Charge Coupled Device." *Nucleic Acids Research*, vol. 22, No. 11, pp. 2121–2125, 1994.

Marshall, et al. "DNA Chips: An Array of Possibilities," *Nature Biotechnology*, vol. 16, pp. 27–31, Jan., 1998.

Ramsay, "DNA Chips: State–of–the–Art," *Nature Biotechnology*, vol. 16 pp. 40–44, Jan., 1998.

European Search Report completed on Dec. 15, 2003, and issued to a related foreign application.

\* cited by examiner

*Primary Examiner*—Carla J. Myers
(74) *Attorney, Agent, or Firm*—Knobbe, Martens, Olson & Bear, LLP

(57) ABSTRACT

A method for separating and collecting nucleic acids, which comprises:
  a step of bringing a sample nucleic acid solution into contact with a nucleic acid-immobilized substrate comprising a substrate and two or more kinds of single-stranded nucleic acids separately immobilized on the substrate, to allow hybridization of the immobilized single-stranded nucleic acids and single-stranded nucleic acids complementary to the immobilized single-stranded nucleic acids, and
  a step of separating the hybridized single-stranded nucleic acids according to immobilized portions of the immobilized nucleic acids, to collect the hybridized single-stranded nucleic acids without disassembling the nucleic acid-immobilized substrate.

10 Claims, 3 Drawing Sheets

SEQUENCE LISTING

<160> NUMBER OF SEQ ID NOS: 6

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Primer for PCR

<400> SEQUENCE: 1

```
caggaaacag ctatgac                                                    17

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Primer for
      PCR

<400> SEQUENCE: 2
gttttcccag tcacgac                                                    17

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
gtaaaacgac ggccagt                                                    17

<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence: Primer for
      PCR

<400> SEQUENCE: 4
accctcacta aagggaa                                                    17

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Primer for
      PCR

<400> SEQUENCE: 5
gtaaaacgac ggccagt                                                    17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
tacgactcac tataggg                                                    17
```

METHOD FOR SEPARATING AND COLLECTING NUCLEIC ACIDS

This application claims the priority JP 2000-021842, filed Jan. 26, 2000.

BACKGROUND OF THE INVENTION

The present invention relates to a method for separating and collecting nucleic acids, which is used for nucleotide sequence determination of nucleic acids, DNA analysis and so forth.

As methods for separating and collecting nucleic acids, the subtraction method, the differential display method and so forth have conventionally been used. Further, Japanese Patent Application Laid-open (Kokai) No. 4-325092 discloses a method for simultaneously collecting two or more kinds of nucleic acids by immobilizing single-stranded nucleic acids having different nucleotide sequences on separable multiple supports respectively, and bringing a sample nucleic acid mixture into contact with the supports to allow hybridization of each immobilized nucleic acid and a single-stranded nucleic acid in the mixture, having a nucleotide sequence complementary to the immobilized nucleic acid.

However, the method described in Japanese Patent Application Laid-open No. 4-325092 suffers from a problem that, since the nucleic acids are separated by separating the supports, kinds of usable supports are extremely limited. Further, since the supports must be separated in order to separate the nucleic acids, the method also suffers from a problem that it is difficult to simultaneously separate many kinds of nucleic acids. Moreover, the method suffers from a problem that separation of many kinds of nucleic acids requires a large amount of sample nucleic acid mixture, and the method also becomes troublesome.

SUMMARY OF THE INVENTION

The present invention was accomplished in view of the aforementioned problems, and an object thereof is to provide a method for separating and collecting nucleic acids that can separate and collect two or more kinds of nucleic acids in a simple manner.

The inventors of the present invention found that if hybridization was performed by using a substrate on which multiple kinds of nucleic acids are immobilized, and the hybridized nucleic acids were each separated and collected directly from the substrate without disassembling the substrate, the nucleic acids can be separated and collected in a simple manner, and thereby the aforementioned object can be achieved. Thus, they accomplished the present invention.

That is, the present invention provides the following.

(1) A method for collecting nucleic acids, which comprises:
a step of bringing a sample nucleic acid solution into contact with a nucleic acid-immobilized substrate comprising a substrate and two or more kinds of single-stranded nucleic acids separately immobilized on the substrate, to allow hybridization of the immobilized single-stranded nucleic acids and single-stranded nucleic acids complementary to the immobilized single-stranded nucleic acids, and a step of collecting each of the hybridized single-stranded nucleic acids separately according to immobilized portions of the immobilized nucleic acids, without disassembling the nucleic acid-immobilized substrate.

(2) The method according to (1), wherein the nucleic acid-immobilized substrate is a substrate carrying a compound having a carbodiimide group.

(3) The method according to (1) or (2), wherein the nucleic acid-immobilized substrate is a DNA microarray.

(4) The method according to any one of (1) to (3), wherein the substrate has a plate-like shape.

DETAILED DESCRIPTION OF THE INVENTION

Figure 1:
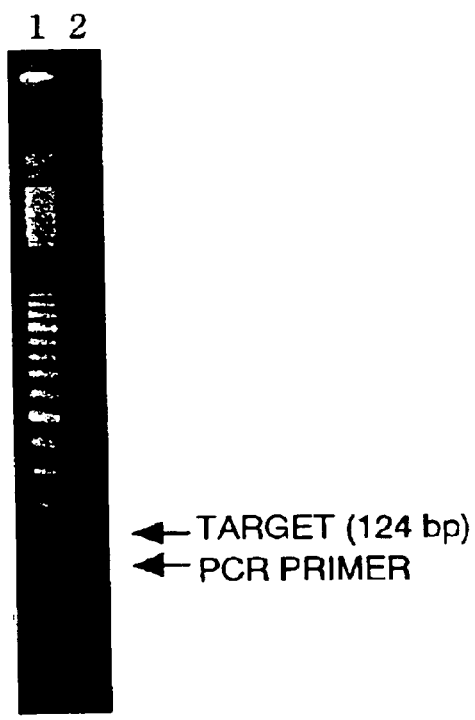
FIG. 1 shows results of amplification of a target by PCR in Example 1 according to the present invention.

Hereafter, embodiments of the present invention will be explained.

<Nucleic Acid-immobilized Substrate>

The nucleic acid-immobilized substrate used for the method for separating and collecting nucleic acids of the present invention, comprises a substrate and two or more kinds of single-stranded nucleic acids immobilized on the substrate, which nucleic acids usually have known sequences.

The substrate used for the present invention plays a role of immobilizing nucleic acids, and it is not particularly limited so long as it is basically composed of a material that is insoluble in a solvent and is in a state of solid or gel at an ordinary temperature or within a temperature range around it (usually 0 to 100° C.). The expression that the substrate is insoluble in a solvent means that the substrate is substantially insoluble in various aqueous and organic solvents used for process steps where single-stranded nucleic acids are immobilized on the substrate, and it is used in the method for separating and collecting nucleic acids of the present invention as described hereinafter.

Specific examples of the material of the substrate include plastics, inorganic polymers, metals, naturally occurring polymers, ceramics and so forth.

Specific examples of the plastics include polyethylene, polystyrene, polycarbonate, polypropylene, polyamide, phenol resin, epoxy resin, polycarbodiimide resin, polyvinyl chloride, polyvinylidene fluoride, fluorinated polyethylene, polyimide, acrylic resin and so forth. Specific examples of the inorganic polymers include glass, crystal, carbon, silica gel, graphite and so forth. Specific examples of the metals include gold, platinum, silver, copper, iron, aluminum, magnet, paramagnet and so forth. Examples of the naturally occurring polymers include cellulose, chitin, chitosan, alginic acid, derivatives thereof and so forth. Specific examples of the ceramics include apatite, alumina, silica, silicon carbide, silicon nitride, boron carbide and so forth.

The aforementioned substrate may be in the form of, for example, film, plate, fiber etc., and its size is not particularly limited.

As the single-stranded nucleic acids to be immobilized on the nucleic acid-immobilized substrate used for the present invention, naturally occurring or synthetic single-stranded DNA (including oligonucleotides) or RNA (including oligonucleotides) can be used without any particular limitation. The single-stranded nucleic acids to be immobilized on the nucleic acid-immobilized substrate of the present invention may have known sequences or unknown sequences. Although the length of the single-stranded nucleic acids is not particularly limited, it usually has a length of 6 nucleotides to thousands of nucleotides.

Two or more kinds of single-stranded nucleic acids are immobilized in a state that they are separated from each other or one another. The single-stranded nucleic acid immobilized on each of the separated portions may composed of one kind of single-stranded nucleic acid or a mixture of single-stranded nucleic acids. Therefore, the term "two or more kinds" means that the immobilized nucleic acids are different in the nucleotide sequence and/or mixtures constituting the immobilized nucleic acids are different in the composition. Geometrical arrangement of those nucleic acids and so forth may suitably be selected depending on the way of use, purpose of use and so forth of the nucleic acid-immobilized substrate to be obtained.

The single-stranded nucleic acids can be immobilized on the aforementioned substrate by known methods. Examples of the methods include, for example, (i) a method of directly immobilizing single-stranded nucleic acids on the substrate by physical adsorption, (ii) a method of immobilizing the nucleic acids on a substrate originally having groups that can be covalently bonded to amino groups or imino groups with covalent bonds between such groups on the substrate and amino groups or imino groups of the nucleic acids, (iii) a method of immobilizing the nucleic acids on the substrate via a compound that can bond to both of the substrate and the nucleic acids and so forth.

The method of (i) can be carried out by, for example, spotting (dropping) a solution containing the single-stranded nucleic acid on the substrate using a spotter or micropipette and drying the spotted solution.

Examples of the groups that can be bonded to amino groups or imino groups, which are used in the method of (ii), include functional groups such as a hydroxyl group, an amino group, a carboxyl group, an isocyanate group, an isothiocyanate group and a carbodiimide group. As the substrate having such functional groups, a substrate that originally has the aforementioned functional groups, or a substrate into which the aforementioned functional groups are introduced may be used. The single-stranded nucleic acids can be introduced on such a substrate by conventionally known methods, and the method is suitably selected depending on functional groups carried by the substrate.

As the compound that can bond to both of the substrate and the nucleic acids, used in the method of (iii), for example, a compound having a carbodiimide group, a compound having a group that introduces an alkyl group into another compound through a substitution reaction or addition reaction (this group will be also referred to as "alkylation group" hereafter) and so forth can suitably be used. In particular, a compound having a carbodiimide group is preferred. According to this embodiment, since an oligomer can be covalently bonded, the hybridization condition can be selected from a wide range and therefore accuracy of separation by hybridization can be increased. For example, a condition that can separate nucleic acids different by one nucleotide in a mixture thereof can be used.

Examples of the compound having the carbodiimide group (also referred to simply as "carbodiimide compound" hereinafter) include, for example, polycarbodiimides that can be prepared by the method disclosed in Japanese Patent Application Laid-open No. 51-61599, the method of L. M. Alberino et al. (J. Appl. Polym. Sci., 21, 190 (1990)), the method disclosed in Japanese Patent Application Laid-open No. 2-292316 and so forth, low molecular weight carbodiimides including monocarbodiimides, dicarbodiimides and so forth that are synthesized by commonly used production methods of carbodiimides such as dehydration of urea compounds and desulfurization of thiourea compounds and so forth. The aforementioned polycarbodiimides may be partially crosslinked.

Other carbodiimide compounds, for example, carbodiimide compounds of hydrophilicity-imparted type that are prepared by adding polyoxyethylene chains in the intramolecular structure, such as those mentioned in Japanese Patent Application Laid-open Nos. 63-172718 and 63-264128 can also be used for the present invention. Further, low molecular weight carbodiimide compounds such as monocarbodiimide compounds and dicarbodiimide compounds are also carbodiimide compounds that can be used for the present invention.

The carbodiimide group in the aforementioned carbodiimide compounds shows high reactivity, and reacts with almost all of active hydrogen groups that are carried by alcohols, amines, thiols, phenols, carboxylic acids and so forth. Therefore, nucleic acids can be firmly immobilized on the substrate via the carbodiimide compound by utilizing the reactivity of the carbodiimide group.

The compound having the alkylation group is used as an alkylation reagent, and examples thereof include alkyl halides, dialkyl sulfates, aromatic sulfonic acid alkyl esters, alkyl metal compounds and so forth.

As such an alkylation reagent, nitrogen yperites can be preferably used. Nitrogen yperites can be produced by the methods disclosed in U.S. Pat. Nos. 2,141,090, 5,273,991, 5,387,707 and so forth.

Specific examples of the nitrogen yperites include halogenated alkyl-N-alkylaminobenzene, dihalogenated alkyl-N-aminobenzene, halogenated alkoxy-N-alkylaminobenzene, dihalogenated alkoxy-N-aminobenzene, halogenated alkyl-N-alkoxyaminobenzene, halogenated alkoxy-N-alkoxyaminobenzene, halogenated alkylphenylaminobenzene, halogenated alkoxy-N-sulfonylalkylaminobenzene, halogenated alkyl-N-sulfonylalkoxyaminobenzene, halogenated alkyl-N-carboxyalkylaminobenzene, halogenated alkoxy-N-carboxyalkylaminobenzene, halogenated alkoxy-N-carboxyalkoxyaminobenzene and so forth.

The aforementioned nitrogen yperites may have another functional group or atom as a substituent. Specific examples of such a substituent include, for example, functional groups such as a hydroxyl group, a halogen atom, a halogenated alkyl group, a halogenated acyl group, a halogenated allyl group, an acyl group, an allyl group, a carboxyl group, a sulfoxyl group, a phosphonium group, a ketone group, an aldehyde group, an isocyanate group, an isothiocyanate group, a carbodiimide group, a thiol group, an amino group and so forth.

The position of the aforementioned substituent may be any position that does not inhibit the alkylation reaction by the nitrogen yperite. Specifically, it may be at a position other than the position of the alkylation group that participates in the alkylation reaction and the position on the tertiary nitrogen atom. The substituent is preferably introduced on an aromatic ring.

In the present invention, nucleic acids can be immobilized on the substrate via the carbodiimide compound or the alkylation reagent by, for example, preparing a substrate carrying the carbodiimide compound or the alkylation reagent and immobilizing the nucleic acids on the substrate utilizing the reactivity of the carbodiimide group of the carbodiimide compound or the alkylation group of the alkylation reagent.

As for the method for obtaining the substrate carrying the carbodiimide compound or the alkylation reagent, the carbodiimide compound or the alkylation reagent may be carried simply by utilizing physical adhesion, or may be chemically carried through a covalent bond. However, in the nucleic acid-immobilized substrate used for the present invention, the carbodiimide compound or the alkylation reagent is preferably carried on the substrate through a covalent bond.

As the carbodiimide compound used in the case where the aforementioned carbodiimide compound is carried on the substrate by utilizing physical adhesion, macromolecular compounds among the aforementioned carbodiimide compounds can be used without any particular limitation. The molecular weight thereof is usually 1000 or more, and preferably 100000 or less.

When the aforementioned alkylation reagent is carried on the substrate by utilizing physical adhesion, there can be used a compound comprising the aforementioned alkylation reagent bonded to a macromolecular compound through a covalent bond (also referred to as "alkylation reagent macromolecular compound" hereinafter). Although such a compound is not particularly limited so long as it is a compound comprising the aforementioned alkylation reagent bonded to a macromolecular compound, it preferably has a molecular weight of 500 to 1000000.

When the carbodiimide macromolecular compound or the alkylation reagent macromolecular compound is carried on the substrate by using physical adhesion, they are typically carried in the form of a coated film. For providing the carbodiimide macromolecular compound or the alkylation reagent macromolecular compound carried on the aforementioned substrate as a coated film, there can be used known methods such as spraying, dipping, brushing, stamping, vapor deposition, and coating using a film coater.

The method for obtaining the substrate carrying the carbodiimide compound through the covalent bond will be explained. The carbodiimide compound to be carried on the substrate through the covalent bond may be any type of the aforementioned carbodiimide compounds.

To obtain the substrate carrying the aforementioned compound having the carbodiimide group on its surface through the covalent bond, for example, a carbodiimide compound having a carbodiimide group for immobilizing nucleic acids when it is carried on the substrate, and further having a functional group for forming a covalent bond with the substrate surface can be covalently bonded to a functional group of the substrate having, on its surface, functional groups that can be covalently bonded to the functional group of the carbodiimide compound by a suitable method.

More specifically, the substrate carrying the carbodiimide compound can be obtained by, for example, covalently bonding a compound having two or more carbodiimide groups or having one or more carbodiimide groups and one or more functional groups other than the carbodiimide group to a functional group of a substrate having, on its surface, functional groups that can be covalently bonded to the carbodiimide group or the functional group other than the carbodiimide group, with at least one of the carbodiimide groups of the compound left.

When the alkylation reagent carried on the substrate through the covalent bond is used, the alkylation reagent may be any one of the aforementioned alkylation reagents. The alkylation reagent carried by the substrate through the covalent bond preferably has 3 to 300 alkylation groups in the molecule. If the number of the alkylation groups is 3 to 300, more preferred ability to immobilize nucleic acids can be obtained, and its solution may have an appropriate viscosity and thus preferred in view of handling thereof.

To obtain the substrate carrying the aforementioned alkylation group through the covalent bond on its surface, for example, an alkylation reagent having an alkylation group for immobilizing nucleic acids when it is used in the nucleic acid-immobilized substrate, and further having a functional group for forming a covalent bond with the substrate surface can be covalently bonded to a functional group of the substrate having, on its surface, functional groups that can be covalently bonded to the functional group of the alkylation reagent by a suitable method.

More specifically, such a substrate can be obtained by, for example, covalently bonding a compound having two or more alkylation groups or having one or more alkylation groups and one or more functional groups other than the alkylation group to a functional group of substrate having, on its surface, functional groups that can be covalently bonded to the alkylation group or the functional group other than the alkylation group, with at least one of the alkylation groups of the compound left.

As the substrate for carrying the aforementioned carbodiimide compound or the alkylation regent, which has, on its surface, functional groups that can be covalently bonded to a carbodiimide group or a functional group of the compound other than the carbodiimide group or an alkylation group or a functional group of the reagent other than the alkylation group, there can be mentioned, for example, substrates into which the functional groups that can provide covalent bonds are introduced on its surface. The functional group to be introduced is not particularly limited so long as it is a functional group that can be covalently bonded to the carbodiimide group or the functional group of the compound other than the carbodiimide group, or a functional group that can be covalently bonded to the alkylation group or the functional group of the reagent other than the alkylation group. Specific examples thereof include a hydroxyl group, an imino group, an amino group, a carboxyl group, a carbodiimide group, an aldehyde group and so forth. These functional groups can suitably be selected depending on the functional group of the aforementioned carbodiimide compound or the alkylation reagent, which is involved in the covalent bond, and they can be introduced onto the substrate surface in a known manner.

To immobilize single-stranded nucleic acids on the substrate via the carbodiimide compound or the alkylation reagent, two or more kinds of single-stranded nucleic acids can be provided on portions where the carbodiimide compound or the alkylation regent is carried under a suitable condition so that the carbodiimide compound or the alkylation reagent and the nucleic acids are brought into contact with each other to cause the reaction between them. As a result of the reaction of the carbodiimide group of the carbodiimide compound or the alkylation group of the alkylation reagent carried by the substrate and an amino group, an imino group or the like of the nucleic acids, the nucleic acids are covalently bonded to the carbodiimide compound or the alkylation reagent. If thiol groups are introduced into the nucleic acids beforehand, a covalent bond is also formed by reaction of the carbodiimide group or the alkylation group and the thiol group. As a result, the nucleic acids are immobilized on the substrate.

Specifically, nucleic acids are usually provided in a state that they are contained in water or buffer so that the activity of the nucleic acids to be immobilized is maintained during the contact reaction of the both. In general, the temperature for the contact is preferably 0 to 100° C. so that the activity of the nucleic acids to be immobilized is not be lost.

In the present invention, means for providing the nucleic acids, usually in the form of water or buffer containing the nucleic acids, on the substrate includes method of utilizing a dispenser, method of utilizing a pin, method of utilizing bubble jet and so forth. However, the present invention is not limited to these.

In the method for separating and collecting nucleic acids of the present invention, a sample nucleic acid solution is brought into contact with the nucleic acid-immobilized substrate so that single-stranded nucleic acids on the nucleic acid-immobilized substrate and single-stranded nucleic acids complementary thereto are hybridized. In order to prevent non-specific binding of nucleic acids and so forth other than the aforementioned immobilized nucleic acids to an unreacted carbodiimide group of the carbodiimide compound or an unreacted alkylation group of the alkylation reagent carried on the substrate, after the nucleic acids are immobilized on the substrate as described above, free carbodiimide or alkylation groups are preferably blocked by bringing the substrate into contact with an excessive amount of bovine serum albumin (BSA), casein, salmon sperm DNA or the like.

The nucleic acid-immobilized substrate may also be used as a DNA microarray (DNA chip). In this case, two or more kinds of single-stranded nucleic acids are spotted in a size and arrangement suitable for use of the nucleic acid-immobilized substrate as a DNA microarray.

<Method for Separating and Collecting Nucleic Acid>

The method for collecting nucleic acid of the present invention comprises a step of bringing a sample nucleic acid solution into contact with the aforementioned nucleic acid-immobilized substrate to allow hybridization of two or more kinds of the single-stranded nucleic acids carried by the nucleic acid-immobilized substrate and single-stranded nucleic acids complementary thereto, and a step of collecting the hybridized single-stranded nucleic acids separately according to immobilized portions of the immobilized nucleic acid, without disassembling the nucleic acid-immobilized substrate.

As the sample nucleic acid solution, a solution containing any of naturally occurring or synthesized DNA (including oligonucleotides) or RNA (including oligonucleotides) can be used without any particular limitation. The sample nucleic acid solution may contain one kind or two or more kinds of nucleic acids.

Various kinds of known methods and reaction conditions can be used for the hybridization. Further, after the hybridization, post-hybridization washing is preferably performed in a known manner to remove non-specifically absorbed nucleic acids prior to the collection of the hybridized single-stranded nucleic acids.

As the method for collecting hybridized single-stranded nucleic acids, various known methods can be used so long as each of the hybridized single-stranded nucleic acids can be separately collected according to immobilized portions of the immobilized nucleic acids without disassembling the nucleic acid immobilized substrate. For example, the following methods can be used.

1. Rubbing off only a portion on which the nucleic acids are immobilized, of the nucleic acid-immobilized substrate with a tip of micropipette or the like after the hybridization.

2. Shaving off a portion (dot) on which nucleic acids are immobilized together with a portion of the substrate by using a spotter having a pinpoint deformed into a shovel shape.

3. Filling a pin of a spotter or a capillary pipet with a DNA-denaturing agent such as an alkali solution, and bringing a tip of the pin or the capillary pipet into contact with dots on the nucleic acid-immobilized substrate in which nucleic acids desired to be collected are hybridized to denature the nucleic acids and transfer the nucleic acids into the pin or the capillary pipet. The nucleic acids can be collected by immersing the pin or the capillary pipet into another solution, or physically transferring the nucleic acids in the pin or the capillary pipet into another container.

Alternatively, the nucleic acids may be denatured by dropping the denaturing agent onto the dots of the nucleic acid-immobilized substrate. These nucleic acids may be sucked up with a membrane or the like and immobilized on the membrane as they are, or the nucleic acids may be collected by sucking up them with an empty capillary pipet or the like. Further, the nucleic acids may also be collected by using an absorber such as sponge, which is fixed at a tip of a pin.

4. Filling a pin of a spotter or a capillary pipet with water or buffer, bringing a tip of the pin or the capillary pipet into contact with dots on the nucleic acid-immobilized substrate in which nucleic acids desired to be collected are hybridized, and heating the substrate in that state, or dropping water or buffer onto the dots and heating the substrate to denature the nucleic acids. The denatured nucleic acids are collected in the same manner as the above 3.

5. Fixing a tip of a capillary pipet filled with water, buffer or DNA denaturant on an electroconductive material. Bringing the tip of the capillary pipet into contact with the dots of the nucleic acid-immobilized substrate, which is also made of an electroconductive material, and applying an electric potential difference between the electroconductive material and the substrate of the nucleic acid-immobilized substrate to collect the nucleic acids into the capillary pipet. If the capillary pipet is filled with water or buffer, the substrate is slightly heated.

If the nucleic acid are collected by using any of the aforementioned methods, each of the nucleic acids can be collected with a high separation accuracy in a simple manner without disassembling the nucleic acid-immobilized substrate, i.e., without cutting the nucleic acid-immobilized substrate, even when two or more kinds of nucleic acids hybridized on the nucleic acid-immobilized substrate are separated and collected.

The method for separating and collecting nucleic acids of the present invention described above can be used for, for example, the following applications.

1. Preparation of library based on information of expression frequency: mRNAs extracted from two or more kinds of samples such as a tumor tissue and normal tissue, of which difference of expression frequency is desired to be detected, are each hybridized, and hybridized samples are separately collected only from dots that showed different detection results. Cloning after preparation of cDNA or PCR utilizing an adaptor as for the nucleic acid collected from a dot (one dot or combined multiple dots) detected only for the tumor tissue as a gene specifically expressed in the tumor tissue enables collection of the gene specifically expressed in the tumor tissue with significantly high possibility (or preparation of a library highly possibly containing the gene). Further, similar cloning or PCR as for the nucleic acid collected from a dot detected only for the normal tissue enables collection of a gene of which expression is specifically prevented by the tumor with high possibility (or preparation of a library highly possibly containing the gene).

Even for a gene expressed in both of the tumor cells and normal cells, if difference is observed in the expression amount for the dots, the gene can be cloned (or a library can be prepared therefor) as genes with different expression frequencies by separately collecting them from each dot. For example, a library of gene (genes) expressed in tumor cells in an amount 5 times as much as that in normal cells can be prepared.

2. Preparation of library based on nucleotide-substituted sequence such as SNPs: if DNA (oligomer) to be immobilized on the nucleic acid-immobilized substrate is selected so that information on nucleotide substitution can be obtained, and hybridization and collection of hybridized DNA are performed, a library of actually existing SNPs and so forth can be prepared.

3. Preparation of library based on information of database such as information of promoter sequences: if DNA to be immobilized on the nucleic acid-immobilized substrate is selected so that information on genes, partial sequences of EST, promoter sequences, regulator genes and so forth retrieved from databases and so forth are provided, presence of the gene can be determined, and the gene can be collected, if present. If the nucleic acid-immobilized substrate is not used, individual investigation of sequences of which existence is unknown requires a large amount of sample, and therefore it is practically difficult.

4. Preparation of library chip: the product collected from the nucleic acid-immobilized substrate can be directly immobilized on a chip (membrane etc.) without cloning and so forth to prepare a library chip or the like. For example, a library chip of genes specifically expressed in a normal tissue and a library chip of genes specifically expressed in a tumor tissue can be prepared from a product collected from the nucleic acid-immobilized substrate, and then mRNA of the gene expressed in the tumor tissue administered with a drug is hybridized thereto to detect efficacy of the drug. The collected nucleic acids may or may not contain a known nucleotide sequence.

When the collected nucleic acids contain a known nucleotide sequence, such a library chip as mentioned above can be prepared from nucleic acids collected from the nucleic acid-immobilized substrate, and hybridized with a labeled probe having a nucleotide sequence of a location different from that of capture oligomer sequence, and presence or absence of signal can be detected to confirm a target substance in a manner simpler than the determination of nucleotide sequence.

As described above, by using the method for separating and collecting nucleic acids of the present inventions, it is possible to separate and collect multiple kinds of nucleic acids in a simple manner, and it becomes possible to directly separate and collect multiple kinds of nucleic acids immobilized on a nucleic acid-immobilized substrate from the nucleic acid-immobilized substrate. Further, it also becomes possible to directly determine the nucleotide sequences of the collected nucleic acids. For these reasons, the risk of taking a nucleic acid for another nucleic acid having a similar nucleotide sequence can be obviated.

Moreover, by using the method for separating and collecting nucleic acids of the present invention, it becomes possible to directly immobilize collected nucleic acids on a solid phase, and perform investigation by hybridization. Furthermore, by using the method for separating and collecting nucleic acids of the present invention, nucleic acids having unknown nucleotide sequences can be extremely efficiently collected and cloned.

EXAMPLES

The present invention will be explained more specifically with reference to the following examples. However, the present invention is not limited only to these examples.

Example 1

(1) Preparation of Oligonucleotides

Oligonucleotides having the nucleotide sequences shown as SEQ ID NOS: 1 to 3 were prepared by using a DNA synthesizer (these oligonucleotides are also referred to as "Oligomers 1 to 3" hereinafter). The oligonucleotide having the nucleotide sequence shown as SEQ ID NO: 3 was synthesized to have an amino linker at its 5' end.

(2) Production of DNA-immobilized Substrate

A solution containing Oligomer 3 produced in the above (1) was spotted on a substrate for immobilizing DNA (slide glass) by using a spotter or a micropipette. When the spotter was used, the DNA solution was spotted in three kinds of sizes having a diameter of about 75 μm, 250 μm and 350 μm. When the micropipette was used, the DNA solution was spotted in two kinds of amounts of 0.5 μl/spot and 3 μl/spot. After the spotting, the substrate was sufficiently dried to prepare a DNA-immobilized substrate.

(3) Amplification of Target by PCR

A partial fragment of pUC119 DNA was amplified by PCR (polymerase chain reaction) utilizing Oligomer 1 and oligomer 2 as primers. Sterilized water in an amount of 12.8 μl was placed in a PCR tube, and 1 μl each of Oligomer 1 (100 μmol/μl), oligomer 2 (100 μmol/μl) and pUC119 DNA (10 ng/μl), 2 μl each of PCR buffer (Takara Shuzo Co., Ltd.) and dNTP (dATP, dGTP, dCTP and dTTP, each at 2.5 mM), and 0.2 μl of Taq enzyme (Takara Shuzo Co., Ltd.) were added thereto. PCR was performed by using a PCR apparatus. The conditions of PCR were as follows.

[Conditions for PCR]
(i) Heat denaturation: 95° C., 30 seconds
(ii) Annealing: 57° C., 25 seconds
(iii) Polymerase reaction: 72° C., 30 seconds After PCR was completed, 1 μl of the amplified sample was subjected to 2% agarose gel electrophoresis to confirm the amplification by PCR (124 bp). The results are shown in FIG. 1. In FIG. 1, Lane 1 shows the results for kb markers and Lane 2 shows the results for the PCR amplification sample, respectively.

(4) Hybridization

The target amplified by PCR in the above (3) in an amount of 3 μl and a hybridization solution (ArrayIt™, Telechem International, Inc.) in an amount of 12 μl were placed in an Eppendorf tube, heated at 100° C. for 5 minutes, and then cooled on ice for 5 minutes to make the target single-stranded. This target solution was dropped onto the DNA-immobilized substrate, covered with cover glass, and left at 42° C. for 1 hour.

(5) Post-hybridization Washing

The DNA-immobilized substrate was immersed in 50 ml of the 2×SSC solution having the following composition for 5 minutes, and then the solution was discarded. The substrate was further immersed in 50 ml of fresh 2×SSC solution to remove the excessive target that did not hybridize from the DNA-immobilized substrate.

[Composition of 2×SSC Solution]

| | |
|---|---|
| NaCl | 1.753 g |
| Trisodium citrate dihydrate | 0.882 g |
| Water | Amount giving a total volume of 100 ml |

(6) Collection of DNA from DNA-immobilized Substrate

A portion on which Oligomer 3 was spotted was rubbed with a tip end of a pipet to collect the hybridized DNA. A portion on which Oligomer 3 was not spotted was also rubbed with a tip end of a pipet (a portion close to the spot and a portion a little away), and used as a negative control.

(7) Confirmation of DNA Collection

Figure 2:
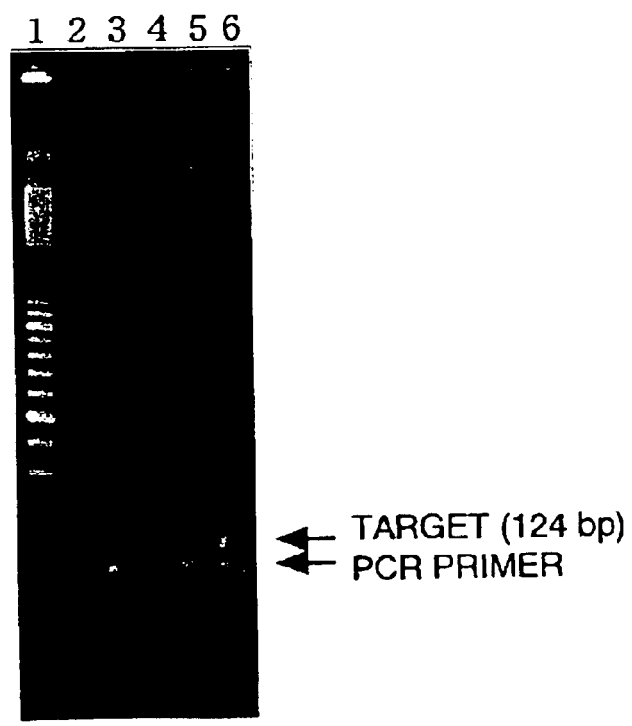
FIG. 2 shows results of confirmation of DNA collection in Example 1 according to the present invention.

The tip of the pipet that was used for the DNA collection was immersed in 12.8 µl of sterilized water contained in a PCR tube, and rubbed against the inner wall of the tube several times to transfer the collected DNA into the sterilized water. To the sterilized water, 2 µl each of Oligomer 1 (100 µmol/µl) and Oligomer 2 (100 µmol/µl), 2 µl each of PCR buffer (Takara Shuzo Co., Ltd.) and dNTP (2.5 mM each), and 0.2 µl of Taq enzyme (Takara Shuzo Co., Ltd.) were added, and PCR was performed by using a PCR apparatus. Then, 1 µl of the amplified sample was subjected to 2% agarose gel electrophoresis, and the amplification by PCR (124 bp) was confirmed based on the spots for all of the sizes of the DNA spotting. The results are shown in FIG. 2. In FIG. 2, there are shown only the results for the spot having a diameter of 75 µm spotted by the spotter (Lane 2) and the spot spotted in an amount of 3 µl/spot by the micropipette (Lane 3).

When PCR and electrophoresis were performed in the same manner for the tip of the pipet used for rubbing the portion on which Oligomer 3 was not spotted, the PCR amplification (124 bp) was not confirmed. The results are also shown in FIG. 2. In FIG. 2, Lane 4 shows the result for a portion close to the spot, Lane 5 shows the result for a portion a little away and Lane 6 shows the result for the PCR amplification sample obtained in the above (3).

Example 2

(1) Preparation of Oligomers

Oligonucleotides having the nucleotide sequences shown as SEQ ID NOS: 1 to 6 were prepared by using a DNA synthesizer (these oligonucleotides are also referred to as "Oligomers 1 to 6", hereinafter). Each of the oligonucleotides having the nucleotide sequences shown as SEQ ID NOS: 3 and 6 was synthesized to have an amino linker at its 5' end.

(2) Production of DNA-immobilized Substrate

Solutions containing Oligomer 3 or Oligomer 6 produced in the above (1) were spotted on a substrate for immobilizing DNA (slide glass) by using a spotter or a micropipette. When the spotter was used, the DNA solutions were spotted in three kinds of sizes having a diameter of about 75 µm, 250 µm and 350 µm. When the micropipette was used, the DNA solutions were spotted in two kinds of amounts of 0.5 µl/spot and 3 µl/spot. After the spotting, the substrate was sufficiently dried to prepare a DNA-immobilized substrate.

(3) Amplification of Target by PCR

A partial fragment of pUC119 DNA was amplified by PCR (polymerase chain reaction) utilizing Oligomer 1 and oligomer 2 as primers. Sterilized water in an amount of 12.8 µl was placed in a PCR tube, and 1 µl each of Oligomer 1 (100 µmol/µl), Oligomer 2 (100 µmol/µl) and pUC119 DNA (10 ng/µl), 2 µl each of PCR buffer (Takara Shuzo Co., Ltd.) and dNTP (dATP, dGTP, dCTP and dTTP, each at 2.5 mM), and 0.2 µl of Taq enzyme (Takara Shuzo Co., Ltd.) were added thereto. PCR was performed by using a PCR apparatus. The conditions of PCR were as follows.

Figure 3:
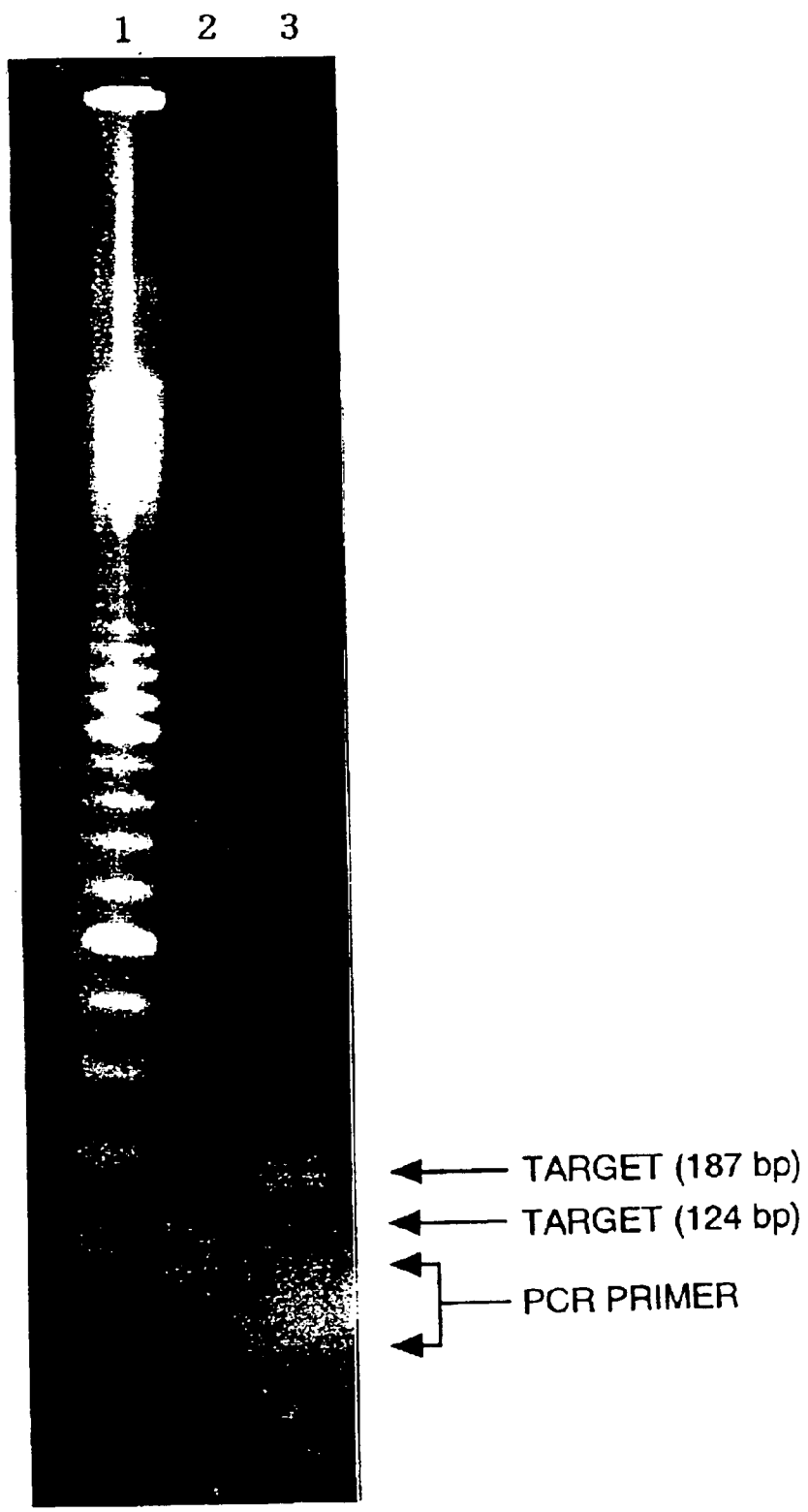
FIG. 3 shows results of amplification of a target by PCR in Example 2 according to the present invention.

[Conditions for PCR]
(i) Heat denaturation: 95° C., 30 seconds
(ii) Annealing: 57° C., 25 seconds
(iii) Polymerase reaction: 72° C., 30 seconds After PCR was completed, 1 µl of the amplified sample was subjected to 2% agarose gel electrophoresis to confirm the amplification by PCR (124 bp). The results are shown in FIG. 3 (Lane 2). In FIG. 3, Lane 1 shows the results for kb markers.

Further, a partial fragment of pbluescript II SK (STRATAGENE) was amplified by PCR utilizing oligomer 4 and Oligomer 5 as primers. Sterilized water in an amount of 12.8 µl was placed in a PCR tube, and 1 µl each of Oligomer 4 (100 µmol/µl), Oligomer 5 (100 pmol/µl) and pBluescript II SK (10 ng/µl), 2 µl each of PCR buffer (Takara Shuzo Co., Ltd.) and dNTP (dATP, dGTP, dCTP and dTTP, each at 2.5 mM), and 0.2 µl of Taq enzyme (Takara Shuzo Co., Ltd.) were added thereto. PCR was performed by using a PCR apparatus. The conditions of PCR were as follows.

[Conditions for PCR]
(i) Heat denaturation: 95° C., 30 seconds
(ii) Annealing: 57° C., 25 seconds
(iii) Polymerase reaction: 72° C., 30 seconds After PCR was completed, 1 µl of the amplified sample was subjected to 2% agarose gel electrophoresis to confirm the amplification by PCR (187 bp). The results are shown in FIG. 3 (Lane 3). In FIG. 3, Lane 1 shows the results for kb markers.

(4) Hybridization

The targets amplified by PCR in the above (3) (124 bp and 187 bp) in an amount of 1.5 µl each were mixed in an Eppendorf tube, and 12 µl of a hybridization solution (ArrayIt™, Telechem International, Inc.) was added thereto. The mixture was heated at 100° C. for 5 minutes, and then cooled on ice for 5 minutes to make the target single-stranded. This target solution was dropped onto the DNA-immobilized substrate, covered with cover glass, and left at 42° C. for 1 hour.

(5) Post-hybridization Washing

The DNA-immobilized substrate was immersed in 50 ml of the 2×SSC solution having the same composition as in Example 1 for 5 minutes, and then the solution was discarded. The substrate was further immersed in 50 ml of fresh 2×SSC solution to remove the excessive target that did not hybridize from the DNA-immobilized substrate.

(6) Collection of DNA from DNA-immobilized Substrate

Each portion on which Oligomer 3 was spotted was rubbed with a tip end of a pipet to collect the hybridized DNA. Each portion on which Oligomer 6 was spotted was also rubbed with a tip end of another pipet to collect the hybridized DNA. A portion on which any oligomer was not spotted was also rubbed with a tip end of a pipet, and used as a negative control.

(7) Confirmation of DNA Collection

Figure 4:
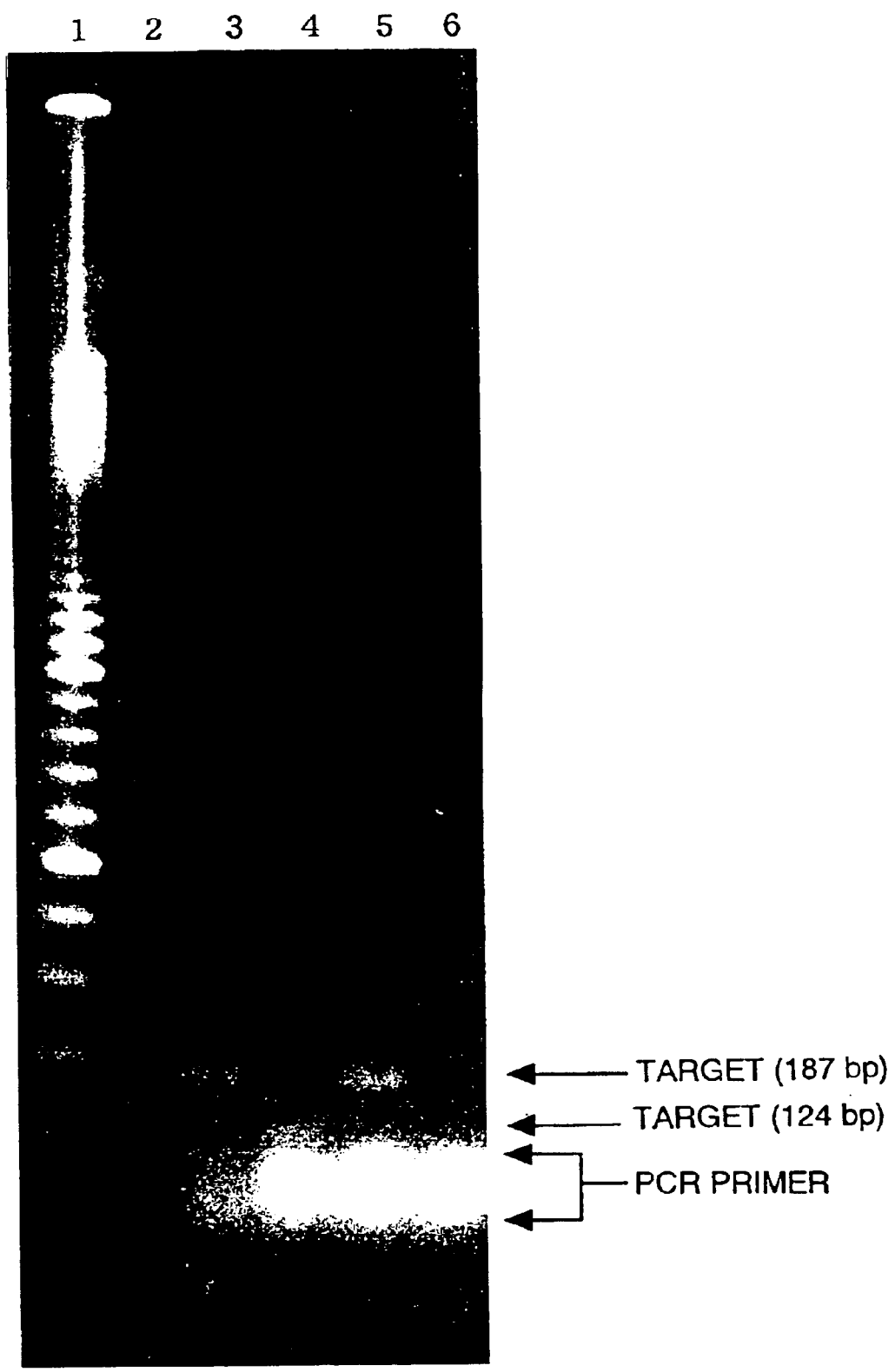
FIG. 4 shows results of confirmation of DNA collection in Example 2 according to the present invention.

Each of the tips of pipets that were used for the DNA collection was immersed in 12.8 µl of sterilized water contained in each of eleven PCR tubes, and rubbed against the inner wall of the tube several times to transfer the collected DNA into the sterilized water. To each sterilized water, 2 µl each of Oligomer 1 (100 pmol/µl), oligomer 2 (100 µmol/µl), Oligomer 4 (100 pmol/µl) and Oligomer 5 (100 µmol/µl), 2 µl each of PCR buffer (Takara Shuzo Co., Ltd.) and dNTP (2.5 mM each), and 0.2 µm of Taq enzyme (Takara Shuzo Co., Ltd.) were added, and PCR was performed by using a PCR apparatus. Then, 1 µl of each amplified sample was subjected to 2% agarose gel electrophoresis. The results are shown in FIG. 4 in parts. In FIG. 4, Lane 1 shows the results for kb markers, Lane 2 shows the results for the PCR amplification sample of the partial fragment of pUC119 DNA (124 bp), Lane 3 shows the results for the PCR amplification sample of the partial fragment of pBluescript II SK (187 bp), Lane 4 shows the results for the PCR amplification sample of DNA collected from the spotted portion of 75 µm in diameter by the spotter of Oligomer 3 on the DNA immobilized substrate, Lane 5 shows the results for the PCR amplification sample of DNA collected from the spotted portion of 75 μm in diameter by the spotter of Oligomer 6 on the DNA immobilized substrate, and Lane 6 shows the results for the PCR amplification sample of the negative control.

The PCR amplification of the target DNA of the hybridization (124 bp) was confirmed on the Oligomer 3-immobilized spots for all of the sizes. In this case, PCR amplification of the DNA of 187 bp was not confirmed. Further, the PCR amplification of the target DNA of the hybridization (187 bp) was confirmed on the Oligomer 6-immobilized spots for all of the sizes. In this case, PCR amplification of the DNA of 124 bp was not confirmed. As for the tip of the pipet used for rubbing the portion on which any oligonucleotide was not spotted, any of the PCR amplifications (124 bp and 187 bp) was not confirmed. Thus, it was confirmed that multiple kinds of DNA hybridized to the DNA-immobilized substrate could be separated on the chip into each DNA and collected.

Example 3

(1) Preparation of carbodiimide Compound Solution 4,4'-Dicyclohexylmethane diisocyanate in an amount of 117.9 g and cyclohexyl isocyanate in an amount of 12.5 g were allowed to react at 180° C. for four days in a nitrogen atmosphere in the presence of 1.3 g of carbodiimidation catalyst (3-methyl-1-phenyl-2-phosphorene-1-oxide) to obtain a carbodiimide compound (polymerization degree: 10, number average molecular weight: 2400) as powder at room temperature. This carbodiimide compound in an amount of 10 g was dissolved in 200 ml of dichloromethane to obtain a carbodiimide compound solution.

(2) Production of Aminated Slide Glass

In an amount of 20 ml of 10% (v/v) solution of 3-aminopropyltriethoxysilane in ethanol was added to 180 ml of distilled water and sufficiently stirred. After the solution was adjusted to pH 3 to 4 with addition of 6 N HCl, 15 pieces of slide glass were immersed into the solution and heated at 75° C. for 2 hours. After the heating was finished, the slide glass was pulled up from the solution, and sufficiently washed with distilled water. Then, the slide glass was subjected to a heat treatment at 115° C. for 4 hours to obtain aminated slide glass.

(3) Preparation of Carbodiimidated Slide Glass

Fifteen pieces of the aminated slide glass prepared in the above (2) were immersed in 200 ml of the carbodiimide compound solution obtained in the above (1), pulled up immediately, and dried at 60° C. with heating for 1 hour. Then, the slide glass was washed twice with 200 ml of dichloromethane for 10 minutes, and dried at 40° C. for 2 hours to obtain carbodiimidated slide glass.

(4) Production of DNA-immobilized Substrate

A solution containing oligomer 3 produced in Example 1, (1) was spotted on the carbodiimidated slide glass obtained in the above (3) by using a spotter or a micropipette. When the spotter was used, the DNA solution was spotted in three kinds of sizes having a diameter of about 75 μm, 250 μm and 350 μm. When the micropipette was used, the DNA solution was spotted in two kinds of amounts of 0.5 μl/spot and 3 μl/spot. After the spotting, the substrate was sufficiently dried, immersed in 50 ml of 3% bovine serum albumin (SIGMA) solution in buffer (0.2 M NaCl, 0.1 M Tris-HCl (pH 7.5), 0.05% Triton X-100; hereinafter referred to as "Buffer A") for 5 minutes, washed with a buffer (TE solution) having the following composition, and dried to prepare a DNA-immobilized substrate.

(Composition of TE solution)

| | |
|---|---|
| Tris(hydroxymethyl)aminomethane | 121.14 g |
| Hydrochloric acid | Amount giving pH of 8 |
| Water | Amount giving total volume of 1000 ml |

(5) Hybridization and DNA Collection

Hybridization and DNA collection were performed in the same manner as in Example 1, (4) to (7), except that the DNA-immobilized substrate prepared in the above (4) was used as the DNA-immobilized substrate. As a result, the same results as Example 1 were obtained.

Example 4

(1) Production of DNA-immobilized Substrate

Solutions containing Oligomer 3 or Oligomer 6 produced in Example 2, (1) were spotted on the carbodiimidated slide glass obtained in Example 3, (3) by using a spotter or a micropipette. When the spotter was used, the DNA solutions were spotted in three kinds of sizes having a diameter of about 75 μm, 250 μm and 350 μm. When the micropipette was used, the DNA solution was spotted in two kinds of amounts of 0.5 μl/spot and 3 μl/spot. After the spotting, the substrate was sufficiently dried, immersed in 50 ml of 3% bovine serum albumin (SIGMA) solution in Buffer A for 5 minutes, washed with TE solution, and dried to prepare a DNA-immobilized substrate.

(2) Hybridization and DNA Collection

Hybridization and DNA collection were performed in the same manner as in Example 2, (4) to (7), except that the DNA-immobilized substrate prepared in the above (1) was used as the DNA-immobilized substrate. As a result, the same results as Example 2 were obtained.

What is claimed is:

1. A method for collecting nucleic acids, which comprises:

contacting a sample nucleic acid solution with a nucleic acid-immobilized substrate comprising a substrate and single-stranded nucleic acids having different nucleotide sequences, said single-stranded nucleic acids being each separately immobilized on the substrate, whereby immobilized portions of the immobilized single-stranded nucleic acids are provided on the nucleic acid-immobilized substrate;

hybridizing the immobilized single-stranded nucleic acids and single-stranded nucleic acids contained in the sample nucleic acid solution and complementary to the immobilized single-stranded nucleic acids to form hybridized nucleic acids; and collecting the hybridized nucleic acids separately according to the immobilized portions by a means selected from the group consisting of:
(1) rubbing off the immobilized portions; and
(2) shaving off the immobilized portions,
wherein the single-stranded nucleic acids are immobilized via a covalent bond.

2. The method according to claim 1, wherein the nucleic acid-immobilized substrate is a substrate on which the single-stranded nucleic acids having different nucleotide sequences are immobilized via a compound having a carbodiimide group carried on the substrate.

3. The method according to claim 1, wherein the nucleic acid-immobilized substrate is a DNA microarray.

4. The method according to claim 2, wherein the nucleic acid-immobilized substrate is a DNA microarray.

5. The method according to claim 1, wherein the substrate has a plate shape.

6. The method according to claim 2, wherein the substrate has a plate shape.

7. The method according to claim 3, wherein the substrate has a plate shape.

8. The method according to claim 4, wherein the substrate has a plate shape.

9. The method according to claim 1, wherein the hybridized nucleic acids are collected by rubbing off the immobilized portions.

10. The method according to claim 1, wherein the hybridized nucleic acids are collected by shaving off the immobilized portions.

* * * * *